(12) United States Patent
Liu et al.

(10) Patent No.: US 11,633,087 B2
(45) Date of Patent: Apr. 25, 2023

(54) ENDOSCOPE MANIPULATOR AND METHOD FOR CONTROLLING THE SAME

(71) Applicant: The Chinese University of Hong Kong, Hong Kong (CN)

(72) Inventors: Yunhui Liu, Hong Kong (CN); Chi-Fai Michael Tong, Hong Kong (CN); Fangxun Zhong, Shenzhen (CN); Zerui Wang, Hong Kong (CN); Hiu-man Yip, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 927 days.

(21) Appl. No.: 16/533,866

(22) Filed: Aug. 7, 2019

(65) Prior Publication Data

US 2020/0046441 A1 Feb. 13, 2020

Related U.S. Application Data

(60) Provisional application No. 62/715,388, filed on Aug. 7, 2018.

(51) Int. Cl.
*A61B 1/00* (2006.01)
*A61B 1/005* (2006.01)
*A61B 34/00* (2016.01)
*A61B 34/30* (2016.01)

(52) U.S. Cl.
CPC ...... *A61B 1/00149* (2013.01); *A61B 1/00148* (2022.02); *A61B 34/30* (2016.02); *A61B 34/70* (2016.02); *A61B 1/005* (2013.01); *A61B 2034/301* (2016.02)

(58) Field of Classification Search
CPC ..... A61B 34/70; A61B 34/30; A61B 1/00147; A61B 1/005; A61B 2034/301
See application file for complete search history.

(56) References Cited

U.S. PATENT DOCUMENTS

| | | | | |
|---|---|---|---|---|
| 2010/0225209 A1* | 9/2010 | Goldberg | ............... | G16H 20/40 312/209 |
| 2011/0238079 A1* | 9/2011 | Hannaford | ............. | A61B 34/76 606/130 |
| 2016/0058514 A1* | 3/2016 | Ogawa | ................... | A61B 34/30 600/104 |
| 2016/0066815 A1* | 3/2016 | Mei | ..................... | A61B 1/00193 606/34 |
| 2019/0083187 A1* | 3/2019 | Danitz | ................. | A61N 1/0502 |
| 2019/0142530 A1* | 5/2019 | Thompson | ............. | A61B 34/37 606/130 |
| 2020/0179077 A1* | 6/2020 | Matsuura | ........... | A61B 1/00188 |

* cited by examiner

*Primary Examiner* — Timothy J Neal
*Assistant Examiner* — William B Chou
(74) *Attorney, Agent, or Firm* — Fish & Richardson P.C.

(57) ABSTRACT

An endoscope manipulator for performing robot-assisted endoscope manipulation comprises a movable robot base with a hollow trunk and a vertical lifting joint; a passive joint set with one end mounted to an upper end of the vertical lifting joint, for manually setting an initial pose of the endoscope; an active joint set mounted to another end of the passive joint set, for adjusting pose control of the endoscope intra-operatively; and a compliant endoscope holder mountable to an end-effector of the active joint set, which passively changes to a compliant state upon an external force exceeding a threshold being applied to an endoscopic lens held by the compliant endoscope holder.

24 Claims, 7 Drawing Sheets

ENDOSCOPE MANIPULATOR AND METHOD FOR CONTROLLING THE SAME

CROSS REFERENCE TO RELATED APPLICATION

The application claims priority of U.S. provisional application No. 62/715,388, the entire disclosure of which is incorporated herein by reference for all purposes.

TECHNICAL FIELD

The application relates to endoscope manipulator and method for controlling the endoscope manipulator.

BACKGROUND

Minimally-invasive surgical techniques like endoscopy have been widely performed for its reduced operative trauma and risk for complication to the patients. Cases of laparoscopy (e.g. including hysterectomy, cholecystectomy, etc.) and endoscopy (e.g. orthopaedic surgery, nasal surgery, etc.) are two typical types of minimally-invasive surgeries which are experiencing tremendous expansion probably because its patient-side acceptance keeps rising, and the improvement of examination and diagnosis.

During minimally-invasive surgeries, endoscope is a critical instrument demanded throughout the surgical procedures to allow the surgeon to inspect the interested area tier surgical examination, planning and procedure execution. Endoscope handling is an important task during the surgery which is done either by the primary surgeon or an assistant. Good handling skills may provide better surgical observation from the surgeon for improved surgery performance. However, in minimally-invasive configuration, this is challenging to be executed by human handling. The confined intracorporeal workspace leaves limited moving range for the endoscope which requires great handling precision by the user to avoid unnecessary collision to the patient. Hand tremor is another issue that might lead to instable images on screen and is difficult to be fully eliminated by manual handling. In addition, long-lasting operating time can cause muscular and mental fatigue to the surgeon/assistant during one case.

Recently, robotics has been widely introduced to the operating room. The better precision and durability of tool manipulation compared to manual handling is expected to facilitate surgical procedures with better performance and outcome. In current clinical practice, the robotic surgery is mainly in form of teleoperation, where the robotic system is separated into patient-side slave manipulators and surgeon-side master control console. The manipulation of robot arms at patient side is entirely based on the surgeon's mastering through the control panel using joysticks. However, such configuration requires spatial area around the operating room for robot set-up, and may not be applicable to side-by-side surgery with the surgeon especially when the surgery types are not suitable to be accomplished by a total teleoperated manner due to concerns of tool manipulability, operating workspace, tactile feedback, etc. To take advantages of robotic manipulations upon supervision for more delicate surgeries, there exists potential to develop new surgical robotic system to act as an "assistant" to execute non-critical surgical tasks like endoscope positioning, meanwhile to allow side-by-side configuration with the surgeon for delicate execution Sinus surgery has also evolved from conventional approaches (leaving external incisions on the face, mouth, etc.) to endoscopic surgeries as well. Unlike laparoscopy, in endoscopic sinus surgery, the surgeon has to use nostril as the natural entrance to reach the tools to diseased areas in nasal cavity. The nasoscope is the most important tool to be used during the surgery. The manipulation of the scope lens should be stable to provide steady images and to avoid collision to the patient's nasal cavity. However, the limited size of nasal cavity leaves the workspace extremely cluttered for insertion of multiple tools during procedures. Therefore, precise handling of the endoscope becomes more challenging and requires concentration from the surgeon or assistant, which can be difficult to overcome due to hand tremor. On the other hand, the surgeon normally uses one hand to hold the endoscope, which should be handed over to an assistant when it comes to bimanual procedures. Teleoperation might be a solution to relieve human handling, but the concerns for safety and workspace in nasal cavity during the surgery makes existing teleoperated robotic systems insufficient to handle.

SUMMARY OF INVENTION

In one aspect of the present application, an endoscope manipulator for performing robot-assisted endoscope manipulation is provided, which comprises: a movable robot base with a hollow trunk and a vertical lifting joint; a passive joint set with one end mounted to an upper end of the vertical lifting joint, for manually setting an initial pose of the endoscope; an active joint set mounted to another end of the passive joint set, for adjusting pose control of the endoscope intra-operatively; and a compliant endoscope holder mountable to an end-effector of the active joint set, which passively changes to a compliant state upon an external force exceeding a threshold being applied to an endoscopic lens held by the compliant endoscope holder.

In another aspect of the present application, a method for controlling the endoscope manipulator is provided, which comprises: providing a foot-mounted wireless control interface implemented with a foot gesture control scheme detecting and recognizing foot gestures of the user by the control interface and transmitting the recognized foot gestures to a processor of the endoscope manipulator to generate corresponding moving commands to motion of the active joint set.

DETAILED DESCRIPTION OF EMBODIMENTS

Figure 1:
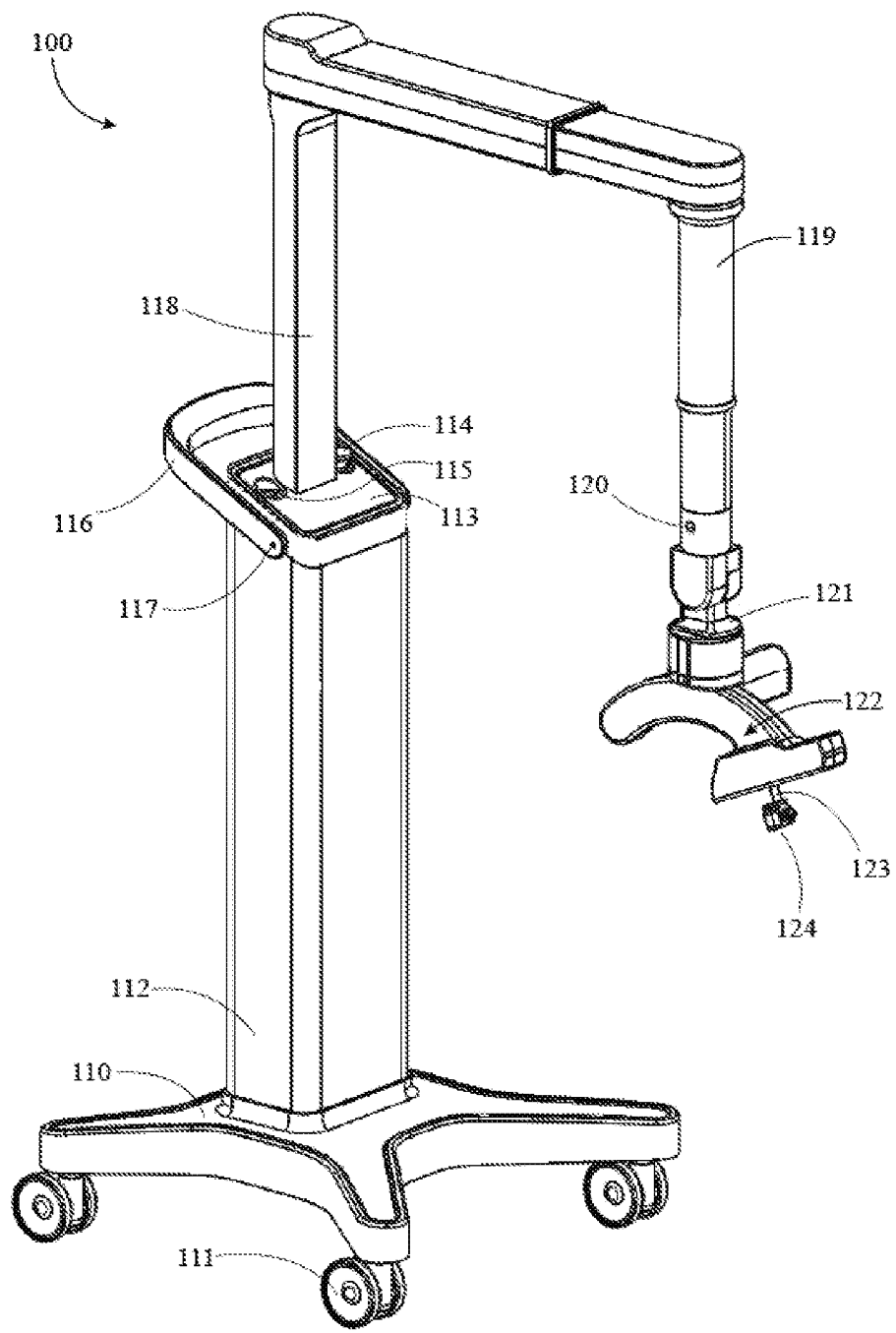
FIG. 1 illustrated a robotic endoscope manipulator which includes a passive set, an active set and a compliant endoscope holder

Reference will now be made in detail to some specific embodiments of the application including the best modes contemplated by the inventors for carrying out the invention. Examples of these specific embodiments are illustrated in the accompanying drawings. While the application is described in conjunction with these specific embodiments, it will be understood that it is not intended to limit the application to the described embodiments. On the contrary, it is intended to cover alternatives, modifications, and equivalents as may be included within the spirit and scope of the application as defined by the appended claims. In the following description, numerous specific details are set forth in order to provide a thorough understanding of the present application. The present application may be practiced without some of these specific details. In other instances, well-known process operations have not been described in detail in order not to unnecessarily obscure the present application.

According to an embodiment of the present application, an endoscope manipulator for performing robot-assisted endoscope manipulation may comprise a movable robot base with a hollow trunk and a vertical lifting joint; a passive joint set with one end mounted to an upper end of the vertical lifting joint, for manually setting an initial pose of the endoscope; an active joint set mounted to another end of the passive joint set, for adjusting pose control of the endoscope intra-operatively; and a compliant endoscope holder mountable to an end-effector of the active joint set, which passively changes to a compliant state upon an external force exceeding a threshold being applied to an endoscopic lens held by the compliant endoscope holder. The movable robot base is configured to support other components of the endoscope manipulator. The passive joint set may be manually adjusted to set and/or lock the initial pose of the endoscope. The active joint set is provided with actuators to respective active joints, which may be controlled during operation to control the pose of the endoscope finely. The compliant endoscope holder has two working states, i.e., a rigid state and a compliant state. The compliant endoscope holder is in the rigid state in default, in which the endoscope lens held by the holder is not movable under an external force. When the external force applied to the endoscope lens exceeds a threshold, the endoscope holder turns to compliant state to protect the patient's nasal cavity. Details of the endoscope manipulator will be discussed below with reference to FIGS. 1-7.

According to the present application, a foot-mounted wireless control interface may be further included. The control interface may be implemented with a foot gesture control scheme. When the control interface is worn on the user's foot, foot gestures of the user are detected and recognized by the control interface and transmitted to a processor of the endoscope manipulator, so as to generate corresponding moving commands to motion of the active joint set. In this way, the endoscope manipulator is controlled in a hands-free manner. Details of the hands-free control will be discussed below with reference to FIG. 8.

FIG. 1 shows a robotic endoscope manipulator 100 designed for functional endoscopic sinus surgery. As shown in FIG. 1, the robot manipulator has a movable robot base 110 whose structure extends radially from the trunk base towards four directions in a webbed shape that forms four ends. An offset distance in horizontal direction may exist between the geometrical centre of the four endpoints of the movable robot base 110 and the centre of gravity of the robot trunk 112. The movable robot base 110 is mounted on four breakable universal wheels 111 mounted underneath the respective extended ends of the movable robot base 110 structure. The breakable wheels are used for automatic position locking of the robot on the floor.

The robot manipulator 100 also includes a robot trunk 112 which stands vertically on the movable robot base 110. The robot trunk 112 may have an I-shape robot backbone and is covered by housing along cuboid faces around the robot backbone which provides an internal hollow structure for enclosing electrical powering and controller components as well as supporting the subsequent joints. The robot trunk 112 may include a slope control panel 113 on the upper surface Who slopes towards the front direction of the robot trunk 112. The slope control panel 113 may further include a normal-close (NC) emergency stop button 114 and a robot power button 115 which are located on respective sides of the slope surface.

An arm lifting apparatus 118 is vertically mounted on the centre of and parallel to the robot trunk 112. The joint body of the arm lifting apparatus 118 passes through the hole of slope control panel 113 and is adjustable along the vertical direction which can further adjust the total height of the robot manipulator 100 through a rod handler. The arm lifting apparatus 118 may comprise a gravity-compensational actuator that provides equivalent forces to make it easier and safer vertical adjustment of the endoscope's height.

The robot trunk 112 may further include a pressing handler 116 which surrounds the surface of the slope control panel 113 whose resting angle can be the same as the sloping surface. The two endpoints of the pressing hander 116 are mounted to a rotatable brake-engaging shaft 117 which is horizontally fixed via a torsion spring with the robot trunk 112 with height approximating the lower position of the surface from slope control panel 113. Braking wires are wrapped around the rotatable brake-engaging shaft 117 and are connected to the four breakable universal wheels 111. Pressing the handler 116 leads to brake releasing, while releasing the pressing handler 116 results in it returning to resting position by the torque applied on the brake-engaging shaft 117 from the torsion spring and engages brakes automatically, which facilitates a "push-and-move" principle for position adjustment of the robot base 110 on the ground.

The robot manipulator 100 may further include the passive joint set 119 may comprise a series of five passive robot joints which are serially structured and mounted at the end of lifting joint 118, forming a cantilever structure to free up an operating space near the robot, while providing five-degree-of-freedom preoperative position and orientation adjustment of the endoscopic lens adjacent to a patient. The five joints in the passive joint set 119 do not have self-actuated motion to joint movements, whose respective joint positions are to be adjusted manually by users. The five joints in the passive joint set 119 are all equipped with normally-engaged magnetic brakes, whose engagement/disengagement are electrically controlled via a single button 120. The single button 120 may lock/unlock all the passive joints with respective magnetic brakes.

Figure 2:
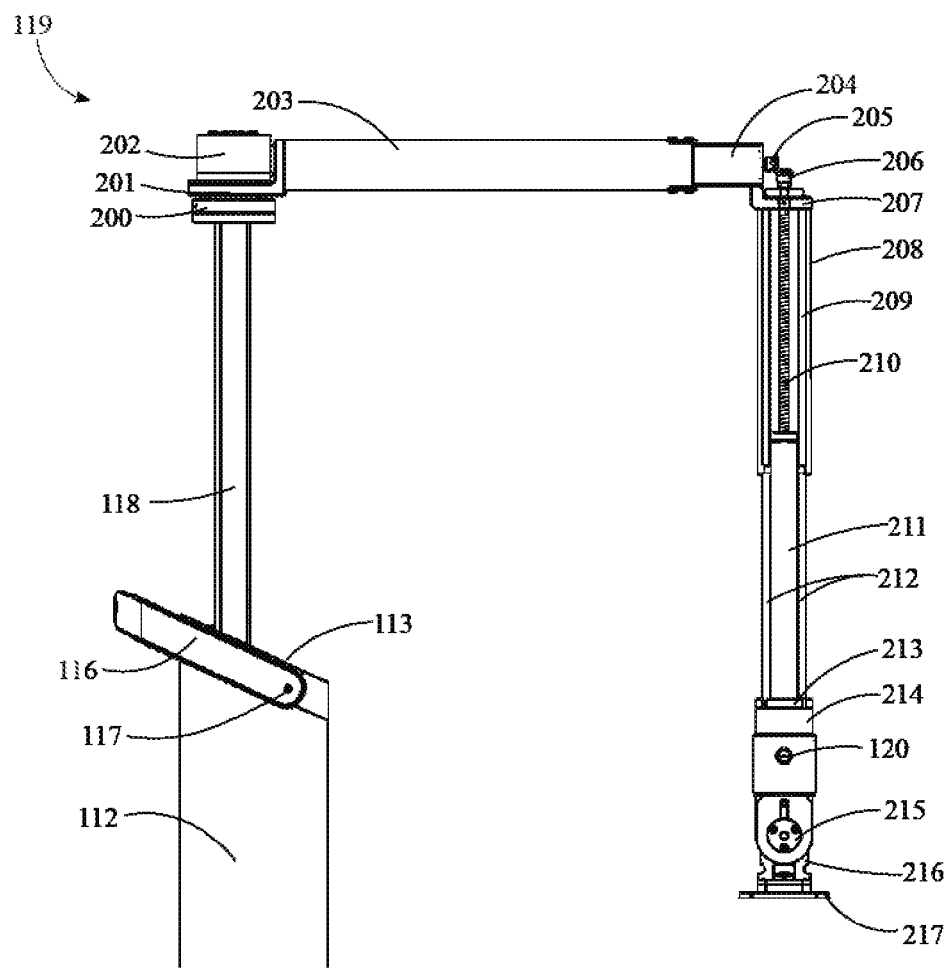
FIG. 2 shows the passive joint set of the endoscope manipulator without housing in side elevation view.

FIG. 2 demonstrates the passive joint set 119. According to the schematic in passive joint set 119, the first passive (revolute) joint may include a ball hearing 200 that connects the lifting joint 118 and the L-shape bracket 201 whose vertical side is further extended by a guide cover 203. A magnetic brake 202 is coaxially connected to the ball bearing 200 via a centre shaft fixed to the lifting joint 118. The guide cover 203 and the movable horizontal linkage 204 forms a prismatic joint that adjusts the horizontally position of the inserting point of the endoscope. A vertical prismatic joint 208 is mounted at the end of movable horizontal linkage 204 via an L-shaped bracket 207. The vertical prismatic joint 208 may further include a hollow guide cover 209 and a vertically movable linkage 211 which mutually forms a ball screw linear guide. A leadscrew 210 is fixed along the geometric centre line of the hollow guide cover 209 and connects to the vertically movable linkage 211 via a ball screw that is located at the tailstock of the hollow link case 209. Note that the structure of the guide cover 209 is buckled with the vertically movable linkage 211 along vertical direction with a 90-degree rotary offset, which share the same cylindrical space for spatial compactness. A pair of guiding rods 212 are fixed in parallel with the vertically movable linkage 211 via the tailstock 213 and move along the guiding grooves inlaid on the guide cover 209. When being passively adjusted, the vertical movement of the movable linkage 211 subject to applied external force backdrives to rotation of leadscrew 210. Additionally, the motor which is equipped with a coaxial magnetic brake on the motor, outputs predetermined output torque to leadscrew 210 through crossed helical gears 205 and 206 to generate equivalent vertical lifting forces to the structure of vertically movable linkage 211 to compensate the gravity load generated by the rest of mechanical structures for easier and safer adjustment of the vertical prismatic joint 208. The passive joint set 119 may further include a revolute joint 214 whose axis is coincided with the vertical prismatic joint 208 and a revolute joint 215 whose axis is horizontally placed. Brake releasing of all passive joints in the passive joint set 119 using the switch button 120 enables the user to freely manipulate the active joint set 122 followed by locking again after completion.

Figure 3A:
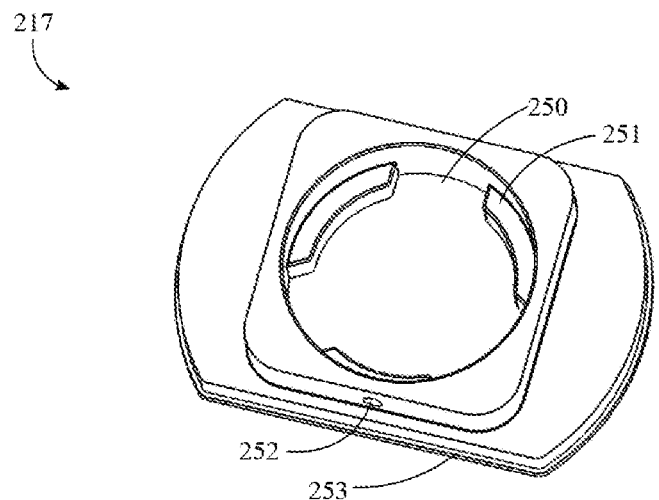
FIGS. 3A and 3B are the illustration of a male plate and a female plate which are the comprising components of the adapter unit.
Figure 3B:
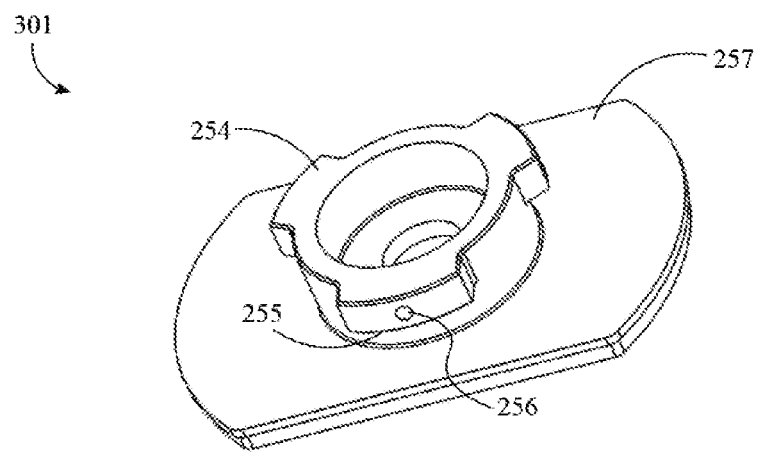

The robot manipulator 100 may further include an adapter unit 121 to mount the active joint set 122 to the passive joint set 119. The adapter unit 121 includes a female plate 217 which comprises a lock ring 251 with a plurality of buckling gaps 250, and a male plate 301 provided with a plurality of buckling teeth 254, as shown in FIGS. 3A and 3B respectively. The shapes of the buckling teeth correspond to the respective buckling gaps 250 but may not share identical sizes circumferentially to allow uniqueness of buckling angle along the ring axis. Inserting the male plate 301 to the female plate 217 via the buckling teeth 254 till the end followed by a relative rotation between two plates leads to position locking of the active joint set 122 to the passive joint set 119, while the remaining rotation degree-of-freedom is further constrained by a screw via the screw hole 252 and 256. The adapter may allow customised design of the active joint set 122 in terms of joint number, structure, etc. for different task implementations, meanwhile remains compatible to the PGP which comprises the robot base 110, the robot trunk 112, the arm lifting apparatus 118 and the passive joint set 119. The adapter unit has a pair of muffling plates that mechanically and electrically connect the active joint set to the passive joint set with a three-step quick installation process: inserting, rotating and screw tightening, which facilitates customised design of the active joint set upon needs and remains compatible to the PGP via the same adapter unit.

Figure 4:
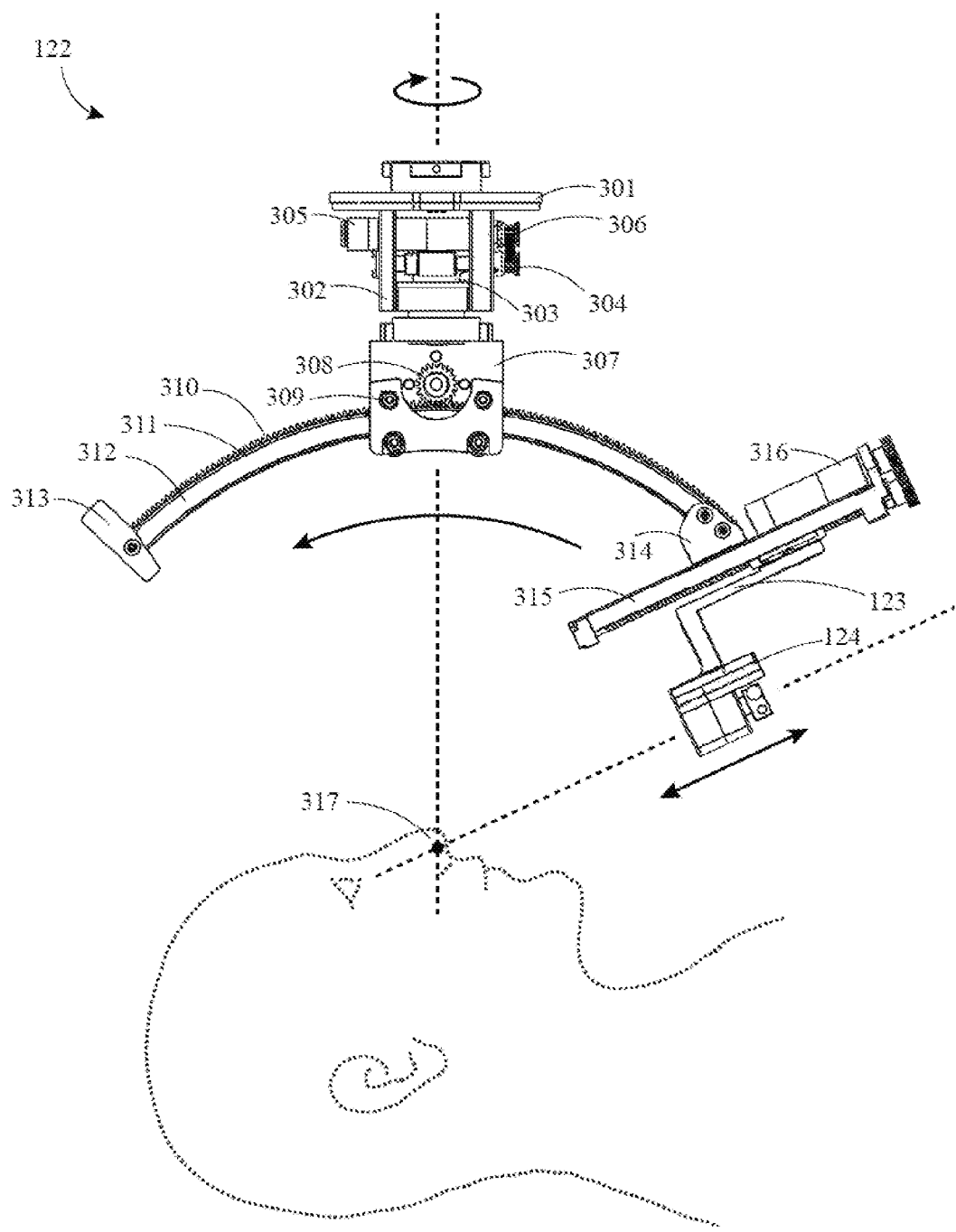
FIG. 4 shows the front elevation view of the active joint set without housing whose structure generates an RCM in operating space, and a set-up configuration to the patient with the respective joint positions arbitrary selected.

The robot manipulator 100 may further include an active joint set 122 with its suggested positioning from the patient shown in FIG. 4, whose three joints are all actuated by corresponding actuators. The first active joint may comprise a compact actuator 305 which is a revolute joint horizontally placed and outputs rotary joint motion along vertical axis via synchronising gears 304 and 306, accompanied by a set of worm gear and wheel 303, which are compactly enclosed to a hollow joint case 302. The bracket 307 connects the structures of the first and second active joint and may include a U-shaped groove for placing the curvilinear gear rack 312. A set of at least four guiding rollers 309 are mounted on the bracket 307 and run on the rolling treads 311 to constrain the curvilinear gear rack 312 (i.e., the second active joint) to rotate along its centre of curvature 317, which rotates with relieved workspace around the patient's head around the centre of curvature 317 for side-by-side operation by the surgeon. The rotation is actuated by a rotary actuator coaxial with shaft 308 via gear transmission to the curvilinear gear 310, whose motion range may be determined by the angle of circumference from the headstock 313 to tailstock 314. The curvilinear gear rack provides a rotation degree-of-freedom whose axis locate remotely from the joint structure, which makes room around the nostril and the patient's head to facilitate the surgeon to parallelly perform surgical procedures side-by-side. The last prismatic joint 315 may comprise a slide actuated by the actuator 316, an L-shaped end-effector 123 mounted on the slide block and an attached compliant endoscope holder 124. The L-shaped end-effector ensures full use of the joint range from the last active joint with the endoscopic lens constantly passing through the remote centre-of-motion. Note that the mounted endoscope lens on the compliant endoscope holder 124 may constantly pass the centre of curvature 317 regardless of respective positions of all the active joints and is named as the remote centre-of-motion (RCM) for the active joint set 122. The RCM may be placed at the nostril of the patient for reduced tip motion of the endoscopic lens inside the nasal cavity. The three active joints are all equipped with actuators which are controllable by the user for manipulation of the mounted endoscope during surgical procedures, and the combined motion of the active joint set forming a remote centre-of-motion which is placed on the patient's nostril for reduced range of movements inside the nasal cavity.

Figure 5:
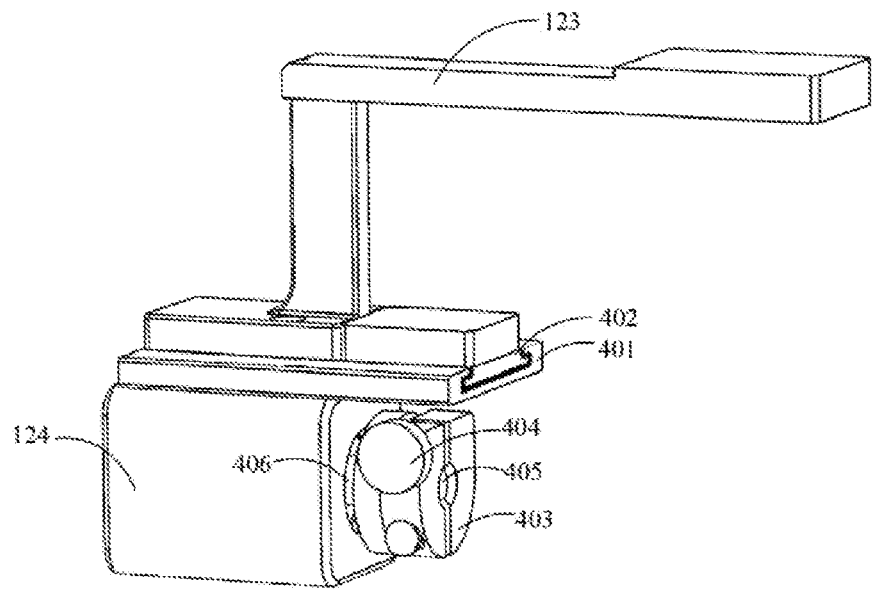
FIG. 5 is the compliant endoscope holder which is shown in weak perspective view that attached to the end-effector on the active joint set.
Figure 6:
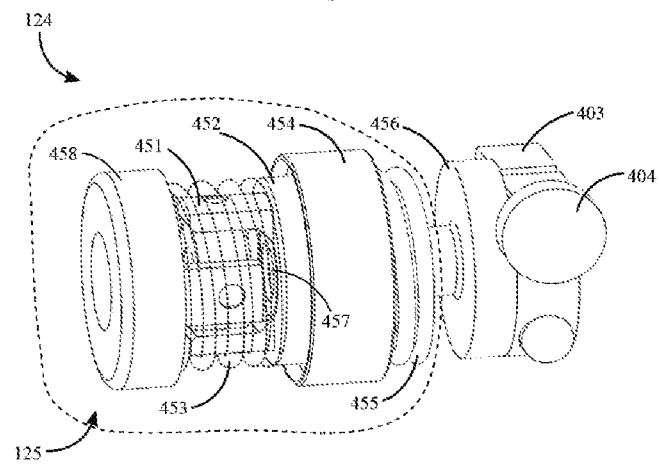
FIG. 6 shows the internal design of the compliant endoscope holder without the joint case.

As shown in FIG. 5, the active joint set may further comprise a compliant endoscope holder 124 mounted on the end-effector of the active joint set 122 via a T-shape sliding slot fixed to the joint case of the compliant endoscope holder 124, which makes the compliant endoscope holder 124 detachable from the end-effector for independent sterilisation by medical staff prior to the surgery. The compliant endoscope holder 124 comprises a mounting slide set which includes the end-effector T-shape sliding slot 401 and the T-shape block 402. The compliant endoscope holder 124 further comprises a compliant joint 125 as shown in FIG. 6 and a lens shaft locking ring including the locking ring 403 and the locking screw 404. Each of the mounting slide set, the compliant joint 125 and the lens shaft locking ring has a hollow shaft to be inserted through by the endoscopic lens. When the external force applied perpendicular to a mounted endoscopic lens exceeds a pre-determined value, a tip of the endoscopic lens becomes movable with the compliant endoscope holder, which becomes the compliant state from a rigid state in which the tip of the endoscopic lens is not movable from external force. In particular, the user aligns and inserts the T-shape block 402 to the end-effector T-shape sliding slot 401 whose position may be automatically locked by a locking bolt underneath the T-shape block 402. By inserting the endoscope via the centre shaft 405 of the compliant end-effector, its axial rotation may be further constrained by tightening the locking screw 404 of the locking ring 403 to complete installation.

As shown in FIG. 6, the compliant joint 125 may comprise an output shaft hub 458 and a friction head 452, which are connected by a universal joint 451 together with a circumferentially mounted tension spring 453 (refer to FIG. 6 in dash line for better illustration). The tension spring 453 is compressed for providing tension force to the universal joint 451 such that its resting position makes the centre hole of the output shaft hub 458 and the guiding hole 457 parallel and concentric in 3D space. The friction head 452 has a rounded cylindrical surface that contacts the surface of the friction plate 454, where a spring 455 is connected to the friction plate 454. An input shaft hub 456 may be further provided whose hollow shaft inserts through the centre hole of the friction plate 454.

The compliant endoscope holder 124 has two working states: the rigid state and compliant state. Once the endoscope is installed, external force applied perpendicular to the axial direction of the endoscopic lens is transformed to the friction force between the friction head 452 and the friction plate 454. If the friction force is lower than the predetermined maximum static friction force, the endoscope remains rigidly fixed to the compliant endoscope holder 124 which the holder works in rigid state. On the other hand, the friction force exceeding the maximum static friction force moves the friction head 452 relative to the friction plate 454 and rotates the endoscopic lens along lateral axis, where the holder works in compliance and allows the lens tip to move with the collided obstacle which might be the nasal cavity of the patient during the surgery. Additionally, the endoscope holder 124 constantly provides passive compliance for axial translation of the endoscopic lens by the spring 455 when longitudinal force is applied externally to the lens shaft.

Figure 7:
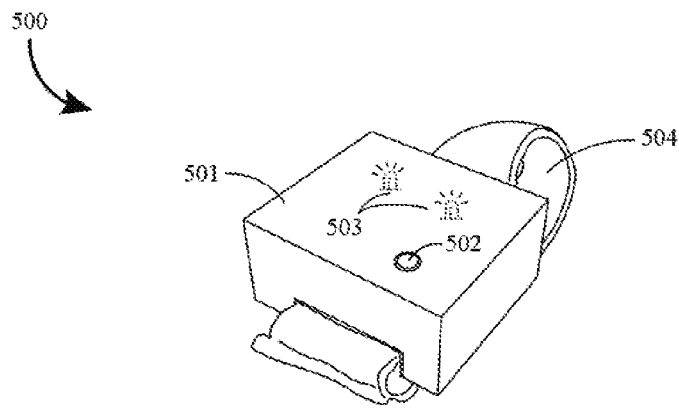
FIG. 7 shows the foot-mounted control interface (not worn by the user) in perspective view with the elastic band laid underneath the housing.

The robot manipulator 100 may also include a foot-mounted control interface 500 which is shown in FIG. 7 for the surgeon to perform hands-free mastering of the robot's active joint set 122 for pose adjustment of the endoscope by the surgeon intraoperatively. The control interface may use Bluetooth for wireless communication to the host controller concerning compatibility of medical devices in the operating room while retaining its mobility during the surgery. The interface may integrate an inertial measuring unit (IMU) to detect the input foot gestures from the surgeon. The electronic components may be enclosed by a cuboid housing 501 using 3D printing and to be mounted to the foot's back via an elastic band 504 which makes the device own a proper wearing direction. The control interface 500 may be further equipped with a power button 502, and two LED indicators 503 with one indicating power and the other indicating connecting status of the device to the host controller which can be observed through the translucent housing 501. The foot-mounted wireless interface is wearable to the user's, either using left or right foot and with either bare foot or on shoes. Using the pre-programmed foot gestures, the user's foot gestures are detected and recognised by host controller PC from the endoscope manipulator to generate moving commands to motion of the active joint set of the endoscope manipulator.

To avoid unexpected control triggering by the surgeon during the surgery, meanwhile to retain adequate sensitivity for control input for easy implementation, the control method from the surgeon via foot gestures towards robotic manipulation of the endoscope with the active joint set 122 may be designed. For example, the foot gesture control scheme provides a set of pre-programmed foot control gestures to allow the surgeon to master the pose of the endoscope in hands-free manner intraoperatively and facilitates the surgeon to perform bimanual surgical procedures parallelly, with a voice indicator that announces the current working status of the active joint set. The control scheme includes enabling/disabling the foot control by doing plantarflexion twice, from which in disabled mode the surgeon is free to move around without risks to move the endoscope by accident. The control scheme includes the changing of currently-controlled joint by doing inversion/eversion of the foot. The control scheme includes moving the joint position of the current joint by plantarflexion followed by swing left/right of the user's heel, which instead of direct heel swinging, to make the control gesture robust to subtle movement while retaining easy implementation. The control scheme allows moving one active joint via a constant velocity at an instant time. All the pre-defined foot control gestures keep the surgeon's wearing foot on the ground without totally airborne, which may contribute to easier balancing of the surgeon's body with minimised physical distraction.

Figure 8:
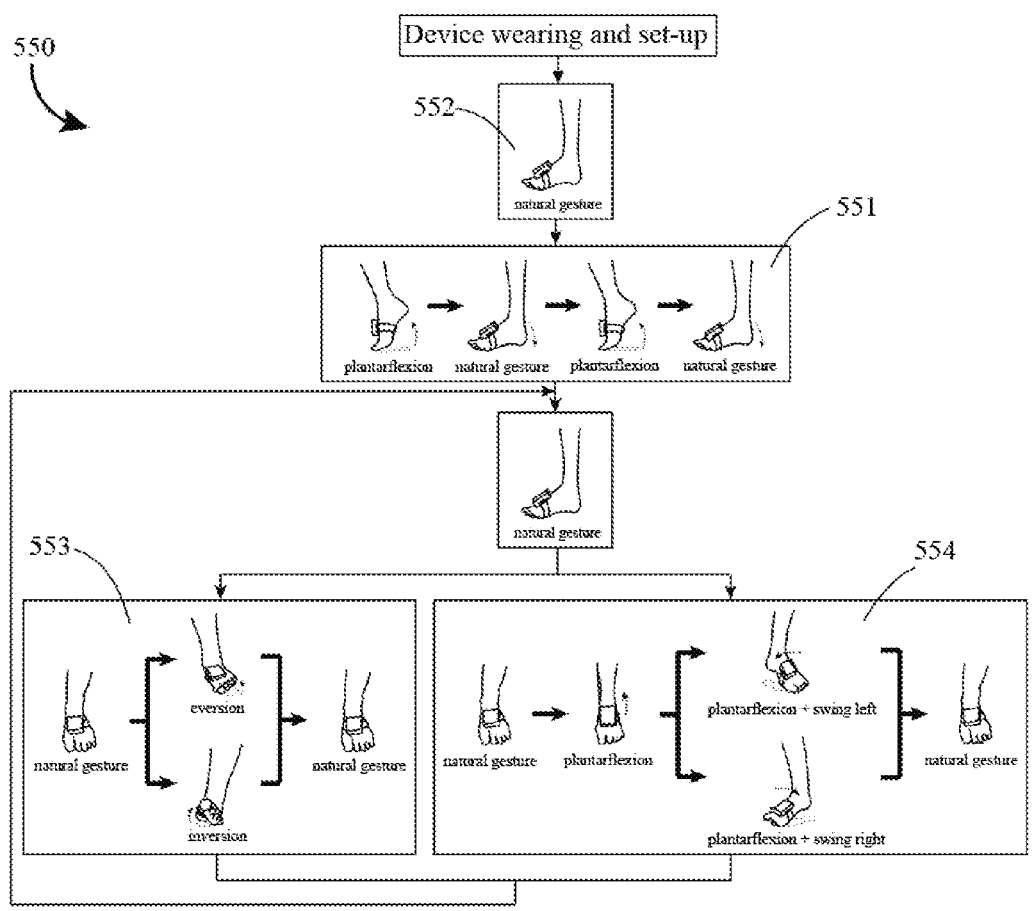
FIG. 8 demonstrates the control scheme of the foot-mounted control interface for controlling the active joint set of the endoscope manipulator in schematic diagram.

FIG. 8 demonstrates the control scheme 550 of the foot-mounted control interface for controlling the active joint set of the endoscope manipulator in schematic diagram. The control scheme 550 as shown in FIG. 8 is introduced when the control interface 500 is worn on but not limited to the user's left foot, and not limited to bare foot wearing.

After the device is properly worn and connected to the host controller, the user may naturally stand on the ground as the step 552, while under this gesture the referenced pose of the control interface 500 is automatically self-calibrated to get ready for foot gesture detection. The control scheme 550 may include a set of foot gestures 551, which further include consecutive plantarflexion motions twice followed by natural standing to enable or disable the foot gesture recognition, from which in disabled mode the surgeon may walk around without risks to move the active joint set 122 accidentally. In enabled mode, the control scheme 550 may further provide a set of foot gestures 553 where the user's foot does inversion/eversion of the foot from natural standing with the purpose of switching the currently-controlled active joint from the active joint set 122; and a set of foot gestures 554 where the user's foot does plantarflexion first followed by a swinging the heel to the left/right to move the currently-controlled active joint in negative/positive direction.

All the pre-defined foot gestures keep the surgeon's wearing foot on the ground without totally airborne, and may be contribute to easier balancing of the user's body. The currently-controlled joint name, the joint's instant moving direction, and the working status of the control interface 500 may be indicated to the surgeon via voice speaker enclosed in the robot trunk 112. Note that the IMU detects the foot gestures from the last self-calibrated referenced pose for command recognition and execution, which may facilitate the user to master the active joint in a hands-free manner without additional intervention.

According to an embodiment of the present application, a method for controlling the endoscope manipulator as described above is also provided. A flowchart of the method is shown in FIG. 9.

Figure 9:
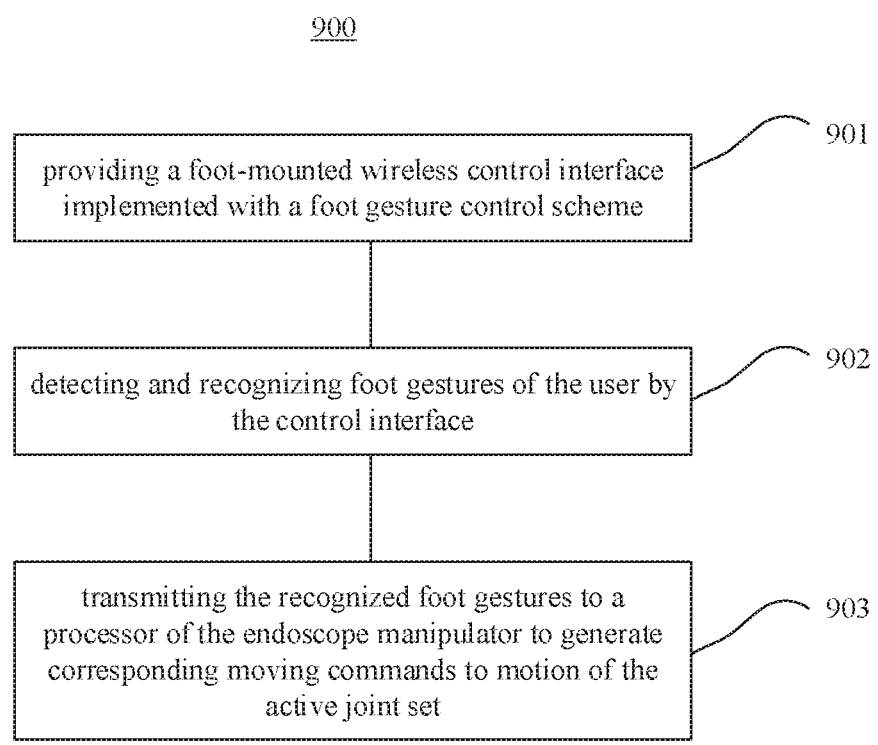
FIG. 9 shows a flowchart of a method for controlling the endoscope manipulator according to an embodiment of the present application.

As shown in FIG. 9, the method 900 for controlling the endoscope manipulator according to the present application includes the following steps. At step 901, a foot-mounted wireless control interface implemented with a foot gesture control scheme is provided. The foot-mounted wireless control interface and the foot gesture control scheme may be the control interface and the control scheme described with reference to FIGS. 7 and 8. At step 902, foot gestures of the user are detected and recognized by the control interface. At step 903, the recognized foot gestures are transmitted to a processor of the endoscope manipulator to generate corresponding moving commands to motion of the active joint set.

Although some embodiments of the present application have been described, those skilled in the art can make variations or modifications to these embodiments upon knowing the basic inventive concept. Although details of the embodiments are described, it is understood that it is not necessary to include all elements in the described embodiments. Instead, some elements in the embodiments could be omitted or altered, without departing from the invention. The appended claims are intended to be considered as comprising the described embodiments and all the variations or modifications fell into the scope of the present application.

The invention claimed is:

1. An endoscope manipulator for performing robot-assisted endoscope manipulation, comprising:
    a movable robot base with a hollow trunk and a vertical lifting joint;
    a passive joint set with one end mounted to an upper end of the vertical lifting joint, for manually setting an initial pose of an endoscope;
    an active joint set mounted to another end of the passive joint set, for adjusting pose control of the endoscope intra-operatively;
    a compliant endoscope holder mountable to an end-effector of the active joint set, which passively changes to a compliant state upon an external force exceeding a threshold being applied to an endoscopic lens held by the compliant endoscope holder; and
    an adapter unit provided between the passive joint set and the active joint set, the adapter unit including a male plate and a female plate for mounting the passive joint set and the active joint set respectively, wherein the adapter unit has a pair of mounting plates that mechanically and electrically connect the active joint set to the passive joint set with a three-step quick installation process: inserting, rotating and screw tightening.

2. The endoscope manipulator of claim 1, wherein the robot base is movable by using a push-and-move handler.

3. The endoscope manipulator of claim 1, wherein the passive joint set comprises:
    five non-actuated serial joints which form a compact cantilever structure to free up an operating space near the robot, while providing five-degree-of-freedom pre-operative position and orientation adjustment of the endoscopic lens adjacent to a patient.

4. The endoscope manipulator of claim 1, wherein the active joint set comprises:
    a revolute joint that uses worm gear and wheel transmission to compact;
    a curvilinear gear rack that provides a rotation relative to a remote centre of curvature; and
    an L-shaped end-effector,
    wherein each of the revolute joint, the curvilinear gear rack and the end-effector is equipped with an actuator which is controllable by a user for manipulation of the endoscopic lens during surgical procedures, and combined motions of the active joint set form a remote centre-of-motion placed on a patient's nostril for reduced movement inside the patient's nasal cavity.

5. The endoscope manipulator of claim 1, wherein the compliant endoscope holder comprises:
    a mounting slide set;
    a compliant joint;
    a lens shaft locking ring;
    wherein each of the mounting slide set, the compliant joint and the lens shaft locking ring has a hollow shaft to be inserted through by the endoscopic lens, when the external force applied perpendicular to a mounted endoscopic lens exceeds a pre-determined value, a tip of the endoscopic lens becomes movable with the compliant endoscope holder, which becomes the compliant state from a rigid state in which the tip of the endoscopic lens is not movable from external force.

6. The endoscope manipulator of claim 5, wherein the mounting slide set further comprises a set of sliding slot and stock with a locking bolt for quick installation and auto-locking of the compliant endoscope holder in position.

7. The endoscope manipulator of claim 5, wherein the compliant joint comprises a set of friction plate and friction head which contact each other to provide a pre-determined maximum static friction force.

8. The endoscope manipulator of claim 5, wherein the compliant joint comprises a universal joint with one side fixed with the friction head and circumferentially mounted by a spring which makes the endoscopic lens rotatable with respect to the endoscope holder, with the universal joint being stretched to 0-degree along lateral direction in natural condition.

9. The endoscope manipulator of claim 5, wherein the lens shaft locking ring includes a hollow shaft and a tightening screw to manually constrain an axial rotation of a shaft of the endoscopic lens inserted therein.

10. The endoscope manipulator of claim 1, further comprising:
    a foot-mounted wireless control interface implemented with a foot gesture control scheme;
    wherein, when the control interface is worn on the user's foot, foot gestures of the user are detected and recognized by the control interface and transmitted to a processor of the endoscope manipulator, so as to generate corresponding moving commands to motion of the active joint set.

11. The endoscope manipulator of claim 10, wherein the control interface is wirelessly communicated with the processor via Bluetooth.

12. The endoscope manipulator of claim 10, wherein the foot gesture control scheme provides a set of pre-programmed foot control gestures to allow the user to master a pose of the endoscopic lens in hands-free manner intraoperatively.

13. The endoscope manipulator of claim 10, wherein the foot gesture control scheme includes enabling/disabling foot control by doing plantarflexion twice.

14. The endoscope manipulator of claim 10, wherein the foot gesture control scheme includes changing currently-controlled joint by doing inversion/eversion of the foot.

15. The endoscope manipulator of claim 10, wherein the foot gesture control scheme includes moving a position of currently-controlled joint by plantarflexion followed by swing left/right of the user's heel.

16. The endoscope manipulator of claim 10, wherein the foot gesture control scheme allows moving one active joint via a constant velocity at an instant time.

17. The endoscope manipulator of claim 10, wherein all pre-defined foot control gestures keep the user's wearing foot on the ground without totally airborne.

18. A method for controlling the endoscope manipulator of claim 1, comprising:
   providing a foot-mounted wireless control interface implemented with a foot gesture control scheme;
   detecting and recognizing foot gestures of the user by the control interface; and
   transmitting the recognized foot gestures to a processor of the endoscope manipulator to generate corresponding moving commands to motion of the active joint set.

19. The method of claim 18, wherein the foot gesture control scheme provides a set of pre-programmed foot control gestures to allow the user to master a pose of the endoscopic lens in hands-free manner intraoperatively.

20. The method of claim 18, wherein the foot gesture control scheme includes enabling/disabling foot control by doing plantarflexion twice.

21. The method of claim 18, wherein the foot gesture control scheme includes changing currently-controlled joint by doing inversion/eversion of the foot.

22. The method of claim 18, wherein the foot gesture control scheme includes moving a position of currently-controlled joint by plantarflexion followed by swing left/right of the user's heel.

23. The method of claim 18, wherein the foot gesture control scheme allows moving one active joint via a constant velocity at an instant time.

24. The method of claim 18, wherein all pre-defined foot control gestures keep the user's wearing foot on ground without totally airborne.

* * * * *